US00PP32373P2

(12) United States Plant Patent
Hansen

(10) Patent No.: US PP32,373 P2
(45) Date of Patent: Oct. 20, 2020

(54) ***PANICUM* PLANT NAMED 'GUNSMOKE'**

(50) Latin Name: ***Panicum virgatum* (L.)**
Varietal Denomination: Gunsmoke

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/873,091

(22) Filed: Jan. 30, 2020

(51) Int. Cl.
*A01H 5/12* (2018.01)

(52) U.S. Cl.
USPC ..... Plt./384

(58) Field of Classification Search
USPC ..... Plt./384
See application file for complete search history.

*Primary Examiner* — Annette H Para

(57) ABSTRACT

A new and distinct plant of ornamental switch grass named *Panicum* 'Gunsmoke' with broad blue-green foliage that retains it coloration into the fall. The upright and dense culms produce tall plant with broadly-spreading airy panicles beginning greyed reddish-purple and becoming tan seed heads that are retained into winter.

1 Drawing Sheet

Latin botanical classification: *Panicum virgatum* (L.).
Variety denomination: 'Gunsmoke'.

STATEMENT REGARDING PRIOR DISCLOSURES UNDER 37 CFR 1.77(B)(6)

The first non-enabling disclosure of the claimed plant, was the photograph and brief description on a website operated by Walters Gardens, Inc. on Feb. 1, 2019. Subsequently the claimed plant was advertised in the "Walters Gardens 19-20 Catalog" distributed beginning May 29, 2019. The claimed plant was first sold on Jul. 8, 2019 by Walters Gardens, Inc., who obtained the plant and all information relating thereto, from the inventor. No plants of *Panicum* 'Gunsmoke' have been sold in this country or anywhere in the world, nor has any disclosure of the new plant been made, more than one year prior to the filing date of this application, and such sale or disclosure within one year was either derived directly or indirectly from the inventor.

BACKGROUND OF THE PLANT

*Panicum* 'Gunsmoke', hereinafter also referred by just the cultivar name 'Gunsmoke' and the "new plant" is a new and distinct cultivar of switch grass. The new plant originated from a cross between 'Apache Rose' U.S. Plant Pat. No. 29,142 and 'Northwind' at a wholesale perennial nursery in Zeeland, Mich. in the late summer of 2014. The seed was collecting in the autumn of 2014 and sown the following spring. The individual seedling was initially selected from among many for further observation in the summer and fall of 2016 at which time it was assigned the breeder code 14-5-7 prior to giving the new plant a cultivar name.

The new plant has been successfully asexually propagated by division since fall of 2016 at the same wholesale perennial plant nursery in Zeeland, Mich. and found to produce stable and identical plants that maintain the unique characteristics of the original plant. The plant is stable and reproduces true-to-type in successive generations of asexual reproduction.

BRIEF SUMMARY OF THE PLANT

*Panicum* 'Gunsmoke' differs from its female parent, 'Apache Rose', in that the new plant is taller and has more blue-green foliage that does not change over the growing season. 'Northwind' is similar in leaf color but is significantly taller in habit.

The nearest comparison varieties known to the inventor are: 'Blue Fountain' U.S. Plant Pat. No. 28,192, 'Apache Rose' U.S. Plant Pat. No. 29,142, 'RR1' U.S. Plant Pat. No. 17,994 and 'Shenandoah'. The new plant is similar in leaf color and form, but is significantly shorter than 'Blue Fountain' and has greyed reddish-purple seed heads before maturing to tan. 'Apache Rose' has more intense red in the seed heads, the leaves and habit are slightly shorter and develop tips of purple in the fall, and the habit is not as dense. The new plant is taller in height than 'RR1' and slightly shorter in height than 'Shenandoah' but both 'RR1' and 'Shenandoah' develop reddish-purple or purplish-red leaf color in July and their habit is different. Table 1 below including includes comparisons of other known *Panicum* cultivars:

TABLE 1

| CULTIVAR | U.S. PLANT PAT. NO. | TOTAL HEIGHT (cm) | INITIAL COLOR | SEASONAL COLOR |
|---|---|---|---|---|
| 'Apache Rose' | Plant Pat. 29,142 | 95 | gray green | purple tipped |
| 'Bad Hair Day' | Plant Pat. 29,313 | 210 | yellow green | yellow green |
| 'Blue Fountain' | Plant Pat. 28,192 | 210 | blue green | blue green |
| 'Cape Breeze' | Plant Pat. 24,895 | 75 | dark green | purple tipped |

TABLE 1-continued

| | | | | |
|---|---|---|---|---|
| 'Cheyenne Sky' | Plant Pat. 23,209 | 112 | blue green | concord purple |
| 'Dallas Blues' | Plant Pat. 11,202 | 193 | grayed blue green | purple tipped |
| 'Gunsmoke' | current application | 135 | blue green | blue green |
| 'Haense Herms' | (not patented) | 100 | green | red purple |
| 'Heavy Metal' | (not patented) | 180 | blue green | blue green |
| 'Hot Rod' | Plant Pat. 26,074 | 90 | blue green | red purple |
| 'Northwind' | (not patented) | 180 | blue green | yellow green |
| 'Prairie Fire' | Plant Pat. 19,367 | 100 | blue green | deep wine |
| 'Rostrahlbush' | (not patented) | 110 | green | red purple |
| 'RR1' | Plant Pat. 17,944 | 120 | blue green | purple-red |
| 'Shenandoah' | (not patented) | 140 | blue green | red purple |
| 'Thundercloud' | Plant Pat. 20,665 | 275 | blue green | blue green |
| 'Totem Pole' | Plant Pat. 29,951 | 200 | blue green | blue green |

| CULTIVAR | SEASON OF CHANGE BEGINNING | HABIT |
|---|---|---|
| 'Apache Rose' | late July | dense upright |
| 'Bad Hair Day' | none | upright |
| 'Blue Fountain' | none | upright |
| 'Cape Breeze' | late September | compact upright |
| 'Cheyenne Sky' | early July | very upright |
| 'Dallas Blues' | late September | upright arching |
| 'Gunsmoke' | none | upright arching |
| 'Haense Herms' | early August | upright |
| 'Heavy Metal' | none | very upright |
| 'Hot Rod' | early spring | upright |
| 'Northwind' | September | upright |
| 'Prairie Fire' | early July | upright |
| 'Rostrahlbush' | early August | upright |
| 'RR1' | early July | compact |
| 'Shenandoah' | late July | arching |
| 'Thundercloud' | none | arching upright |
| 'Totem Pole' | none | columnar |

The following traits of *Panicum* 'Gunsmoke', in combination, have been repeatedly observed in multiple generations of asexually propagated plants and distinguish the new plant from all other switch grass plants known to the inventor:

1. Broad blue-green foliage that retains its coloration into the fall.
2. Upright and dense culms producing tall plants that do not lodge.
3. Broadly-spreading airy panicles beginning greyed reddish-purple and becoming tan seed heads that are retained into winter.

BRIEF DESCRIPTION OF THE DRAWINGS

The photographs of the new plant demonstrate the overall appearance of three-year-old plants growing in an outdoor display garden and a two-year-old plant in the greenhouse in Zeeland, Mich., including the unique traits. The colors are as accurate as reasonably possible with color reproductions. Ambient light spectrum, source and direction may cause the appearance of minor variation in color.

DETAILED BOTANICAL DESCRIPTION

Figure 1:
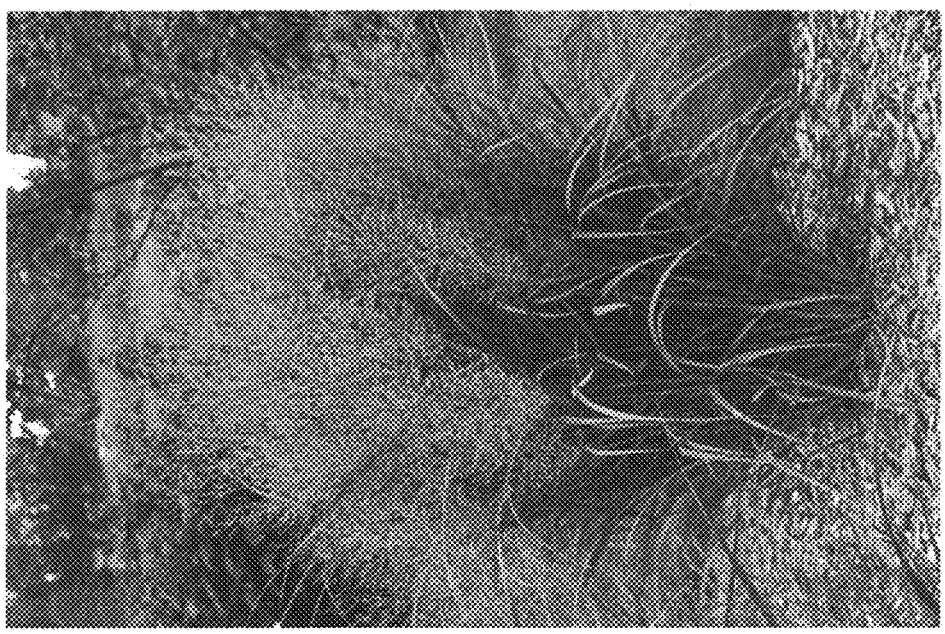
FIG. 1 shows the overall plant in mid-season.
Figure 2:
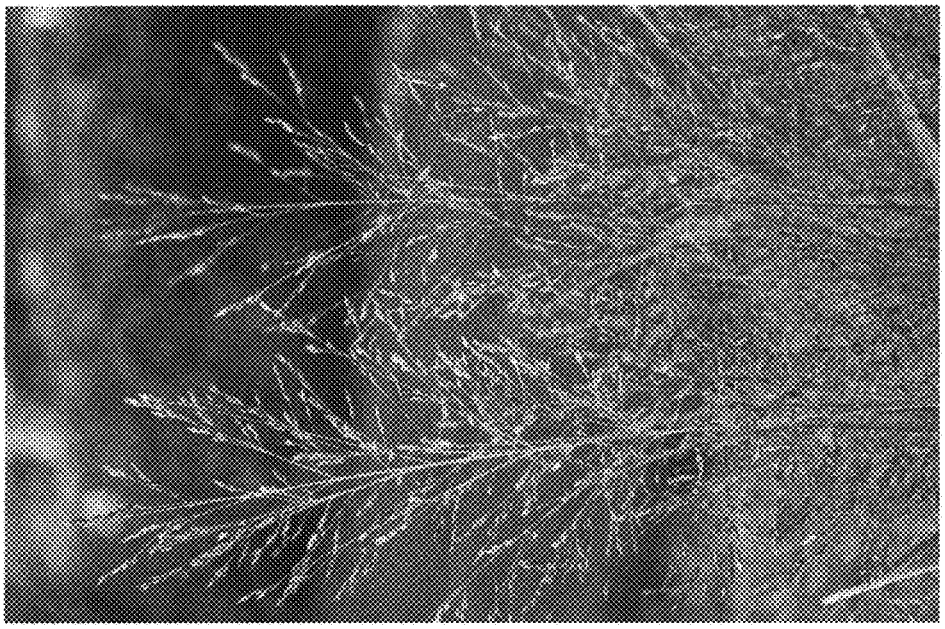
FIG. 2 shows a close-up of the inflorescence in late-July to early-August.

The following descriptions and color references are based on the 2015 edition of The Royal Horticultural Society Colour Chart except where common dictionary terms are used. The new plant, 'Gunsmoke', has not been observed under all possible environments. The phenotype may vary slightly with different environmental conditions, such as temperature, light, fertility, moisture and maturity levels, but without any change in the genotype. The following observations and descriptions are of a three-year-old plant in a loamy-sand trial garden of a wholesale perennial nursery in Zeeland, Mich., USA, grown in full sun with supplemental water and fertilizer as needed.

Parentage: Female (seed parent) 'Apache Rose' times 'Northwind' male (pollen);

Propagation method: By division of the culms;

Time to finishing in a 3.8 liter pot: Rapid; about 7 to 9 weeks from 25 mm diameter plug;

Rooting habit: Normal, coarsely branching; root color nearest RHS 155D;

Plant description:

Plant shape and habit: Hardy herbaceous perennial forming tightly rhizomatous columnar clump, with very upright culms topped with finely-textured airy inflorescence producing a narrow clump about twice as tall as wide;

Plant size: Foliage height at flowering time is about 120.0 cm tall from soil line to the top of the foliage and 135.0 cm tall to top of flowers; about 38 cm wide at soil line and about 90.0 cm at widest point about 90.0 cm above soil;

Foliage description: Glabrous, glaucous; linear; flat; margin with microscopic marginal dentations; sheathed from node of attachment to ligule, adaxial and abaxial surfaces dull; deciduous but persist through winter;

Foliage size: To about 52.0 cm long and about 10.0 mm wide and about 41.5 cm long without sheath; averaging with sheath about 48.0 cm long and 9.0 mm wide; shorter at distal end; typically 6 leaves per culm;

Foliage color: Adaxial between RHS N138C and RHS 189A; abaxial between RHS N138C and RHS 189B; winter adaxial surface more grey than RHS 164D; winter abaxial surface between RHS 199D and RHS 164D;

Veins: Parallel; midrib about 0.5 mm across; abaxial ridged, adaxial slightly recessed;

Vein color: Adaxial and abaxial indistinguishable and same color as surrounding leaf;

Culm: Erect; terete; hollow; glabrous; glaucous; dull surface; about 75% enclosed by leaf sheath; about 150 culms per clump;

Culm dimension: To about 47.0 cm long without panicle, average about 45.0 cm; not including panicle to about 59.0 cm long, average about 53.0 cm long; about 3.0 mm diameter at base; internode length average about 7.5 cm; node width about 4.0 mm;

Culm color: Variable; base nearest RHS N186C with undertone of nearest RHS N138D; mid-section nearest RHS 188C with undertone of between RHS 138A and RHS 138B; top portion nearest RHS 189A;

Node description: About 6 per culm, slightly swollen to about 4.0 mm diameter;

Node color: Nearest RHS 164B;

Flower description: Finely-branched open panicle, one panicle per culm;

Flower timing: Beginning late July, flowering through late August, panicles dry and remain effective through winter;

No flower fragrance detected;

Panicle: Pyramidal, to about 32.0 cm long and 11.0 cm wide; overall effective color nearest RHS 187B;

Rachis: Terete, branched, glabrous, glaucous; about 32.0 cm long and about 2.0 diameter mm at base; branches to about 13.0 cm long and about 1.0 mm diameter held at about 60 degree angle above horizontal; color nearest RHS N138C;

Spikelet: Usually with two florets; about 10.0 mm long;

Rachilla: Thin, terete, stiff to about 8.0 mm long and about 0.2 mm diameter; color nearest and RHS N138C;

Lower glume: About 3.0 mm long and 1 mm wide; without awn; color variable between RHS N187C and RHS 187B;

Lemma: Without bristle; acute apex, truncate base; margin entire; upper and lower both about 3.0 mm long and 0.5 mm wide; color nearest RHS 139D;

Palea: Acute apex, truncate base, margin entire; about 2.0 mm long and 0.7 mm across; translucent, nearest RHS 160D;

Gynoecium: Two;

*Stigma*.—Two, plumose, protruding about 1.5 mm from glume and about 0.5 mm diameter; color nearest RHS 165A.

*Style*.—Thin; about 1.0 mm long and 0.1 mm diameter; color nearest RHS 155D.

*Ovary*.—Ellipsoidal; acute apex, rounded base; about 2.5 mm long and 1.0 mm diameter; color between RHS 148A and RHS 148B.

Androecium: Two or three;

*Filaments*.—Short; hair-like; less than 0.1 mm diameter and up to 1.0 mm long; color nearest RHS NN155D.

*Anthers*.—Two; dorsifixed, longitudinal; about 2.5 mm long and about 1.0 mm wide; color nearest RHS N163A.

*Pollen*.—Round, abundant; less than 0.1 mm in diameter; nearly transparent, color lighter than RHS 155D.

Fruit: Caryopsis; about 2.5 mm long and about 1.0 mm wide; color between and closer to RHS 161C than RHS 199D;

Hardiness, pest and disease resistance: The plant is very drought once established. Hardiness at least from USDA zone 4 through 9. Disease and pest resistance beyond what is typical of that of other switch grasses has not been observed.

I claim:

1. A new and distinct cultivar of ornamental switch grass, *Panicum* plant named 'Gunsmoke', as herein described and illustrated.

* * * * *